United States Patent [19]

Burchiel et al.

[11] E Patent Number: Re. 32,417

[45] **Reissued Date of Patent:* May 12, 1987**

[54] RADIOLABELED ANTIBODY TO ANTI-TUMOR ASSOCIATED ANTIGEN AND PROCESS

[75] Inventors: Scott W. Burchiel; Buck A. Rhodes, both of Albuquerque, N. Mex.; David R. Crockford, Haverhill, Mass.

[73] Assignees: Summa Medical Corporation, Albuquerque, N. Mex.; University Patents Inc., Norwalk, Conn.

[ * ] Notice: The portion of the term of this patent subsequent to Jan. 19, 1999 has been disclaimed.

[21] Appl. No.: 825,367

[22] Filed: Feb. 3, 1986

Related U.S. Patent Documents

Reissue of:

[64] Patent No.: 4,472,371
Issued: Sep. 18, 1984
Appl. No.: 337,314
Filed: Jan. 6, 1982

U.S. Applications:

[63] Continuation-in-part of Ser. No. 89,153, Oct. 29, 1979, Pat. No. 4,311,688.

[51] Int. Cl.[4] ..... A61K 43/00; A61K 49/02

[52] U.S. Cl. ..... 424/1.1; 206/569; 422/61; 424/9

[58] Field of Search ..... 424/1.1, 9; 206/569; 422/61

[56] References Cited

U.S. PATENT DOCUMENTS

| | | | |
|---|---|---|---|
| 3,927,193 | 12/1975 | Hansen et al. | 424/1.1 |
| 4,116,776 | 9/1978 | Dalbow et al. | 436/542 |
| 4,174,385 | 11/1979 | Reid | 424/1.1 |
| 4,311,688 | 1/1982 | Burchiel et al. | 424/1.1 |
| 4,323,546 | 4/1982 | Crockford | 424/1.1 |
| 4,361,544 | 11/1982 | Goldenberg | 424/1.1 |

*Primary Examiner*—Christine M. Nucker
*Attorney, Agent, or Firm*—Berman, Aisenberg & Platt

[57] ABSTRACT

Antibodies to human carcinoembryonic antigen (CEA), human alphafetoprotein (AFP) and/or to other anti-human tumor associated antigens (TAA) labeled with technetium-99m (Tc-99m) are administered to a human after the human has been administered anti-CEA, anti-AFP and/or other anti-TAAs, such as human melanoma-associated antigen, human neuroblastoma-associated antigen, human breast cancer-associated antigen, human ovary-associated antigen, human sarcoma-associated antigen, etc. The biodistribution of the labeled product composition accumulates at cancer sites, e.g., tumors that produce or express TAA, due to the affinity that the antibody has for the given tumor antigen. The accumulation at the tumor site(s) of a suitable amount of Tc-99m associated with the antibody allows detection via external scintigraphy and other means. Detection of the Tc-99m antibody composition by external scintigraphy permits localization and detection of tumors in vivo via a semi-noninvasive technique.

34 Claims, No Drawings

RADIOLABELED ANTIBODY TO ANTI-TUMOR ASSOCIATED ANTIGEN AND PROCESS

Matter enclosed in heavy brackets [ ] appears in the original patent but forms no part of this reissue specification; matter printed in italics indicates the additions made by reissue.

REFERENCE TO RELATED APPLICATIONS

This application is a continuation-in-part of application Ser. No. 089,153, filed Oct. 29, 1979, now U.S. Pat. No. 4,311,688.

BACKGROUND OF THE INVENTION

This invention relates to compositions and methods capable of detecting cancer cells or malignant tumors in humans. More particularly, this invention relates to compositions radiolabeled with technetium-99m (Tc-99m) which, when administered to a human will accumulate at cells producing human carcinoembryonic antigen (CEA), human alphafetoprotein (AFP), other tumor-associated antigens (TAA) and/or mixtures thereof.

The use of compositions which emit radiation at levels which can be detected after administration to the human body are well known. These compositions are utilized to visualize and/or monitor functioning of various parts of the body or are utilized diagnostically to determine the presence or absence of particular cellular and/or tissue antigens, macromolecules, hormones or the like. In one particular aspect of the prior art, radiolabeled antibodies are utilized to detect tumors having associated therewith CEA. As disclosed in U.S. Pat. Nos. 3,663,684, 3,867,363 and 3,927,193, $I^{131}$ or $I^{125}$ labeled antibodies are used to detect human malignancy. Antibodies radiolabeled with $I^{131}$, $I^{125}$ or $I^{123}$ have been used to detect murine teratocarcinomas in an in vivo model (Ballou et al, Science, 206, pp. 844–847, 1979).

It is also well known that various molecular proteins, including glycoproteins, lipoproteins and other types of macromolecules can be associated with certain types of cancers, and as such, these molecules can be considered to be tumor-associated antigens (TAA) (Rosenberg, Serologic Analysis of Human Cancer Antigens, Academic Press, New York, 1980.) Examples of TAA include hCG, CEA, AFP and a variety of antigens that have been defined using polyclonal heterologous and monoclonal antibodies that are associated with melanoma, breast cancer, lung cancer, ovary, sarcoma and other types of cancers.

It is also well known that protein molecules can be tagged with Tc-99m to form diagnostic agents, some of which can be used for in vivo scanning agents that can identify human malignancy (Rhodes et al, Basics in Radiopharmacy, C. V. Mosby, St. Louis, 1978). An example of such a composition is Tc-99m labeled human serum albumin (Tc-99m HSA). However, there is no prior art relating to the use of Tc-99m labeled antibody molecules using the preferred procedure discussed in this application.

With regard to hCG, it has been proposed to tag the antibody of the beta-chain of hCG with peroxidase (McManus et al, Cancer Research, 36, pp. 2367–3481, September, 1976) in order to identify the antigen in malignant tumors in vitro. Furthermore, it has been proposed to label the IgG antibody to hCG with radioactive iodine in order to localize the antigen in human choriocarcinomas transplanted in hamster cheek pouches (Quinones et al, Journal of Nuclear Medicine, Vol. 12, pp. 69–75, 1971).

Recently, it has been found that neoplastic tissues produce and/or express on their surface hCG, hCG-like material and a compound similar to and/or identical to the beta-chain of hCG or mixtures thereof, specifically to the degree where it may be considered to be a more general marker than either CEA or AFP (Acevdo et al, "Detection and Prevention of Cancer", Part 2, Vol. I, H. E. Neiburgs (ED), Marcel Dekker, Inc., New York, 1978, pp. 937–979. The positive identification of hCG in a heterogenous group of cancer cells and its non-detection in non-cancer cells in vitro suggests that it may be a useful tumor marker for in vivo imaging.

While peroxidase-labeled or fluorescein-labeled anti-hCG-beta or anti-hCG antibodies are effective for identifying malignant cells, these labeled compositions are undesirable for in vivo use because they do not allow for visualization by any available scintigraphy detection system and are otherwise undesirable for widespread use because they are simply an in vitro immunohistochemical technique requiring light or electron microscopy of biopsy samples for positive identification. In addition, the use of radiolabeled antibodies in scintigraphy wherein the labeled antibody binds directly to the cancer cell having its corresponding antigen, can cause faint and imperfect imaging of the cancer cell or cells since the antibody usually has a limited number of binding sites. Thus, the cell may only be able to accommodate one radiolabeled antibody molecule on a single antigen site. Thus, the density of the radiolabeled molecule on the cell surface may not be sufficient to permit distinction of the cancer cell from surrounding tissues.

Accordingly, it would be highly desirable to provide a class of labeled antibodies which can be utilized in vivo and which overcomes the disadvantages of the prior art compositions.

SUMMARY OF THE INVENTION

In accordance with this invention, radiolabeled compositions are provided which comprise antibodies to anti-TAA, which antibodies are labeled with radioactive Tc-99m. When using the compositions of this invention to diagnose the presence of cancer cells in a patient, the patient first is administered parenterally anti-TAA to accumulate on the sites of the cancer cells which comprise TAA. The compositions of this invention are administered parenterally. The biodistribution of the labeled compositions is monitored by scintigraphy in order to locate cancer cells or malignant tumors. The present invention provides substantial advantages over the prior art, since the compositions provide for higher sensitivity in detecting cancer cells or malignant tumors of the prior art, the technique can be performed in vivo, and the compositions are more effective than compositions utilizing a single antibody approach. The kit contains two components: (1) anti-TAA and/or derivatives thereof; and (2) antibody against anti-TAA or fragments or derivatives thereof. The kit will contain a suitable reducing agent capable of reducing Tc-99m from Tc (VII) to Tc (IV). Tc-99m is added by the user prior to administration to humans. The kit may also contain a chromatographic column containing a material capable of binding Technetium as the pertechnetate or as a complex of Technetium.

DESCRIPTION OF SPECIFIC EMBODIMENTS

The term anti-tumor associated antigen (anti-TAA) as used herein includes anti-human melanoma associated antigen, anti-human neuroblastoma antigen, anti-human breast cancer associated antigen, anti-human ovary associated antigen, anti-human sarcoma associated antigen, anti-carcinoembryonic antigen, anti-alphafetoprotein antigen or any other antibody to an antigen associated with a malignant tumor either alone or in admixture with each other or with anti-hCG and/or anti-hCG-beta or fragments thereof.

Human chorionic gonadotropin (hCG) is a molecule believed to have a molecular weight ranging from about 35,000 and 38,000. hCG is found in the urine and sera of pregnant women, in patients with trophoblastic tumors, in normal placentas and is produced by certain cell cultures. hCG consists of two noncovalently-bonded alpha and beta-chains having approximate molecular weights of 14,700 and 23,000 respectively. The alpha and beta-chains can be easily dissociated; however, it has been shown that each chain is biologically inactive as a separate entity. The amino acid sequence of the alpha-chain has been shown to have close similarity to the alpha-chain of human luteinizing hormone, human follicle stimulating hormone and thyroid stimulating hormone. The beta-chain has similarity only to the beta-chains of luteinizing hormone and less homology to those of follicle stimulating hormone and thyroid stimulating hormone. The beta-chain is immunologically active in both the intact hormone and as a separate entity. Approximately 30 percent of the molecule is carbohydrate which is constituted by six different monosaccharides: sialic acid, L-fructose, D-galactose, D-mannose, N-acetylglucosamine and N-acetylgalactosamine.

Anti-hCG or anti-hCG-beta serum is obtained by any conventional method such as by immunizing animals such as rabbits, sheep, goats or other suitable species with intact hCG or hCG-beta subunit in order to induce production of the hCG antibody or hCG-beta antibody. Serum then is harvested from the immunized animals and the specific anti-hCG or anti-hCG-beta immunoglobulins then can be obtained in sufficiently pure form such as by affinity chromatography, immunoprecipitation, nonimmune precipitation or the like. In affinity chromatography, for example, an hCG-rich fraction first is isolated such as from pregnant female serum or urine by conventional nonimmune precipitation or immunoprecipitation techniques followed by chromatography on DEAE-cellulose followed by gel filtration on Sephadex G-100 or by another suitable purification technique. The hCG-rich fraction thus obtained is passed onto a column of a cyanogen halide activated or periodate activated gel such as Sephadex, Sepharose or cellulose or another insoluble polysaccharide with carboxyl, polyhydroxyl or N-hydroxylsuccinimide ester functionality in order to chemically attach the hCG by a weak covalent bond to the gel. The serum obtained from the animal then is passed through the column and the anti-hCG or anti-hCG-beta becomes specifically attached to the hCG, its corresponding antigen, in the column while the remainder of the other immunoglobulins and non-specific antigens pass through the column. The anti-hCG or anti-hCG-beta then is recovered from the column by passing an appropriate buffer, e.g. acetate, phosphate or other solutions through the column in order to break the weak covalent bond between the anti-hCG or anti-hCG-beta and the hCG-gel matrix. The anti-hCG-beta or anti-hCG can be obtained in any conventional manner such as by elution with solution or buffer of appropriate ionic strength and pH. $F(ab')_2$ fragments of anti-hCG antibody can be prepared according to conventional methodologies.

Carcinoembryonic antigen (CEA) is a well-known high molecular weight cell surface glycoprotein that is expressed by a variety of human colorectal and lung tumors, and it is often secreted into the serum of patients with malignant disease associated with these types of tumors. CEA is comprised of 50–60% carbohydrate, and it oftentimes exhibits a high degree of molecular heterogeneity in terms of molecular size. Its approximate molecular weight is 175,000–200,000, with an isoelectric point of pH 3–4 and a sedimentation value of 6.2–6.8. CEA is isolated by extraction with perchloric acid or other techniques as described in U.S. Pat. No. 3,865,689, and it is subfractionated by ion exchange chromatography.

Specific antisera or monoclonal antibodies can be made to CEA by immunizing an appropriate animal with a suitable immunization schedule. The antibodies are purified and prepared according to conventional methodologies discussed earlier for hCG. Monoclonal antibodies are prepared by fusion of Balb/c or other mouse spleen cells with one of several murine myelomas that have been rendered sensitive to hypoxanthine, aminopterine and thymidine medium (HAT) according to the method of Köhler and Millstein (Nature, 256, 495–497, 1975). Appropriate murine hybridomas are grown in tissue culture or as an ascites in the peritoneal cavity of Balb/c mice. Antibody is isolated from ascites and/or tissue culture fluid by nonimmune or immune precipitation, followed by purification by gel chromatography. Fragmentation of highly purified anti-CEA antibodies may be conducted by treatment of the protein with pepsin at 37° for 5–12 hours. This peptic digest is then fractionated on a Sephadex G-150 column and the $F(ab')_2$ peak is collected, dialyzed and concentrated. The resultant protein is then prepared for Tc-99m labeling discussed elsewhere.

Alphafetoprotein (AFP) is a serum protein normally found in the fetal circulation during gestation. The protein is an alpha globulin with an appropriate molecular weight of 70,000 and an isoelectric point of 4.7–5.2. The protein is comprised of 4% carbohydrate. AFP is isolated by immunoabsorption followed by isoelectric focusing. Specific antisera or monoclonal antibodies to AFP can be prepared as previously described using a purified AFP extract of a crude AFP preparation of amniotic fluid. $F(ab')_2$ Tc-99m labeled antibodies can be obtained as described herein.

Antibodies to tumor associated antigens (TAA) expressed by human melanoma, breast, ovary, lung, sarcoma and other types of cancer are prepared using either conventional polyclonal or monoclonal antibody technology. Polyclonal heterologous antisera is made to human tumor cells by immunizing an appropriate animal, such as a rabbit, sheep, goat, etc., with an attenuated population of human cancer cells, a semi-purified cell membrane preparation and/or a cell free extract containing membrane antigens. Antisera prepared according to this methodology are rendered semi-specific for certain types of human tumor cells by absorbing out any antibodies that react with noncancerous cells. Thus, normal peripheral blood leukocytes can be incubated with antisera to remove antibodies reactive with normal cells. Following sequential absorptions, the remaining antibodies may show selectivity in reacting with human cancer cells. The type of cancer reactive antisera that is generated is dependent upon the type of human cancer cells used for immunization. Detailed procedures used for this type of antisera preparation are well known and are readily available in the medical literature.

Preparation of monoclonal antibodies can also be performed using routine procedures in which Balb/c mice are immunized with human tumor cells, a tumor membrane preparation or a cell-free extract. The spleen cells from immunized mice are fused with murine myeloma cell lines to form murine hybridomas, as described previously.

Biochemical characterization of membrane tumor associated antigens (TAA) has not progressed to the degree that has been demonstrated for hCG, CEA and AFP. A main limitation to this type of work has been the inability to obtain such TAA in large enough quantities to perform routine biochemical analysis. However, some biochemical work has been performed on these types of antigens. For example, melanoma associated antigens (MAA) have been purified and characterized by some investigators, and they have been found to be large molecular weight glycoproteins. Ferrone and co-workers have described a 94,000 and a 230,000 molecular weight MAA (Imai et al, Tumor Imaging: The Radioimmunchemical Detection of Cancer, Masson Publ., USA, New York, 1981) with Hellstrom et al (Proc. Nat. Acad. Sci., USA, 76:2927-2931, 1979) and Koprowski et al (Proc. Nat. Acad. Sci., USA, 75:3405-3409, 1978) describing distinct sets of MAA. Therefore, there may exist many different types of TAA, even for a given type of cancer. This principle is also illustrated for a variety of other different types of cancer including breast, lung, ovarian, sarcoma, etc. (Rosenberg, supra).

Therefore, a number of different types of antibodies to TAA find application in the present invention, with the common denominator for each of these antibodies being that they react with the secreted and/or expressed product of a human tumor. As an example of the type of process to be utilized for the generation of the present composition, i.e., a Tc-99m radiolabeled antibody or antibody fragment to an anti-CEA or any other anti-TAA or mixtures thereof, the discussion that follows will use the CEA and anti-CEA system as an example. However, it should be understood that the present invention applies to any Tc-99m labeled antibody to an anti-TAA.

After the anti-CEA is isolated, an antibody to anti-CEA, hereinafter referred to as a second antibody, is produced in an animal species other than the species used to produce the anti-CEA, hereinafter referred to as the first antibody by either of the two procedures described below:

(1) An animal of a species different from the species in which the first antibody was produced is immunized with a non-immune IgG fraction (normal IgG) of immunoglobulin from an animal species used in obtaining the first antibody in order to produce a desired second antibody which binds to first antibody or:

(2) Immune IgG fraction (anti-CEA-IgG) from the animal used to produce the first antibody is administered to an animal of a different species to produce a desired second antibody which binds to its first antibody.

The process for obtaining the composition of this invention is illustrated by the following schematic route:

EMBODIMENT 1

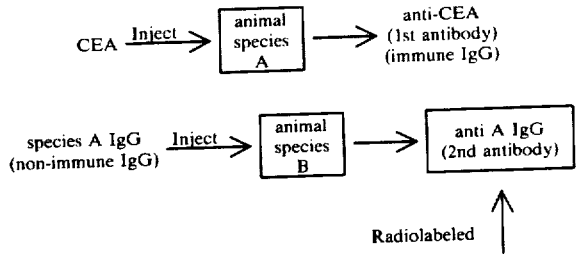

EMBODIMENT 2

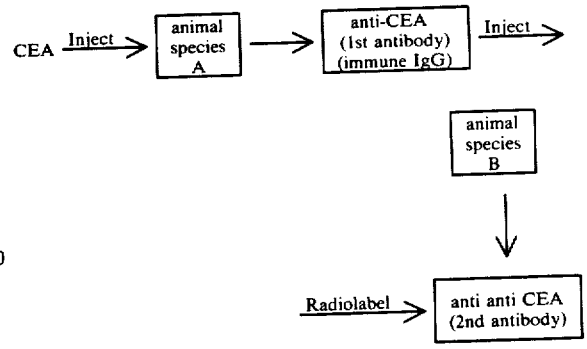

It is to be understood that the above schematic routes are merely exemplary and that any TAA can be utilized initially rather than CEA. Also, it is to be understood that animal species A is not a human. It is preferred to utilize Embodiment 1 because the second antibody produced therefrom will bind specifically to any immune IgG which immunogen (antigen) came from the animal species used to produce the immune IgG. Serum containing second antibody then is harvested and the second antibody is obtained in purified form as for example the procedures set forth above for the anti-CEA.

It is to be understood also that while the present invention is described specifically with respect to the use of two antibodies in series, the present invention is not limited to a series of only two antibodies, the second of which is radiolabeled. In order to provide higher concentrations of the radioisotope located on the cancerous cell, a series of three or more antibodies may be utilized, the last of which is radiolabeled. By operating in this manner, the number of available sites associated with the cancerous cell for attachment of the radiolabeled antibody is increased greatly. The series of suitable antibodies is made as described above, with the only restrictions being that the antibodies adjacent in the series are produced from animal species different from the next adjacent antibodies in the series and that the first antibody produced in the series is anti-CEA. These procedures are shown schematically as Embodiments 3 and 4.

EMBODIMENT 3

-continued

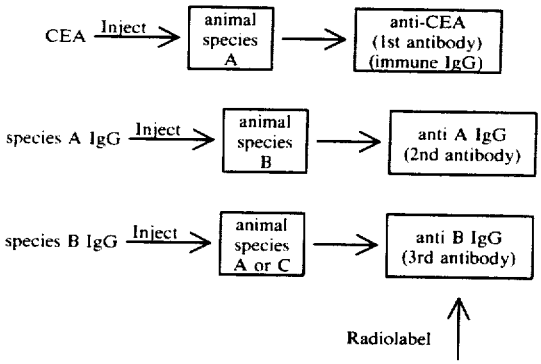

EMBODIMENT 4

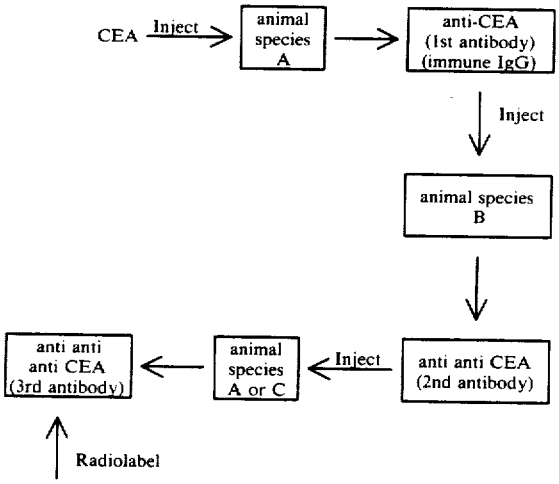

The antibodies are administered parenterally to the patient in the same sequence as they are produced with the radiolabeled antibody being administered last. That is, the first antibody obtained as described above is administered first. Subsequently, the second antibody is administered to produce a third antibody which is radiolabeled. The last antibody in the series of antibodies will be referred to as the "last antibody". The primary limitation on the number of antibodies that are administered is the possibility that the patient will experience undesirable side reactions to the antibodies. The possibility of undesirable side reactions occurring may be reduced by the use of antibody fragments obtained by conventional techniques.

The source of the technetium-99m preferably is water soluble such as the alkali or alkaline earth metal pertechnetate. The technetium can be obtained as sodium pertechnetate Tc-99m from a conventional 99Mo/99mTc generator. Any source of pharmaceutically acceptable technetium-99m may be utilized in the present invention.

The technetium-99m labeled antibody to anti-CEA is prepared by acidic, basic or neutral (ligand-exchange) radiolabeling techniques. In one particular and preferred aspect of this invention, the technetium-labeled antibody to anti-CEA is obtained by a ligand exchange process. In this process, a solution of technetium (IV) is prepared by mixing a solution of technetium such as in the form of a pertechnetate ($TcO_4^-$) and saline with a stannous reducing solution, e.g. stannous fluorideacetate having a pH between about 3 and 5.5. In this procedure, the stannous ions reduce technetium (VII) to technetium (IV). The reduced technetium-99m first is chelated onto the top of a column of Sephadex G-25 (dextran cross-linked with carboxyl functionality) by passing the aqueous solution of technetium-99m through the column. The solution has a pH between about 5.5 and 7.0. The column then is washed with saline to essentially remove free pertechnetate ($TcO_4^-$) or unusual species of technetium thereby leaving the technetium-99m chelated or absorbed or otherwise bound to the column. A physiologic solution of the antibody to anti-CEA then is prepared with appropriate buffer so that the resultant solution has a pH between about 6 and 9, preferably between about 7 to 8. When operating within this pH range, denaturation of the antibody to anti-CEA is eliminated or minimized. The protein is then added in a minimum volume to the top of the column where the technetium-99m/Stannous complex is bound and where it is allowed to stand until the technetium-99m is bound to the protein having stronger bonding sites than the column material. This usually occurs within about 30 minutes. The column then is washed to remove the labeled antibody to anti-CEA. Washing can be effected with a known volume of human serum albumin diluted with 50/50 ACD or the like followed by a known volume of saline. In this manner, the volume of washing saline solution containing the labeled protein can be determined and the labeled protein can be collected. Impurities in the antibody to anti-CEA will remain on the column or will be eluted at a rate different from that of the labeled, immunologically intact, antibody to anti-CEA.

A most preferred method for forming technetium-99m labeled antibody to anti-CEA (or any other TAA) comprises direct labeling of the protein. In this method, a buffered solution is admixed with an acidic solution of $SnCl_2$ which is a reducing agent for pertechnetate. The buffered solution can comprise sodium and /or potassium phthalate, tartrate, gentisate, acetate, borate or mixtures thereof having a pH of between 4.5 and 8.0, preferably about 5.5. Tartrate is utilized to maintain the appropriate concentration of stannous ion in solution to effect the desired solution pH. The $SnCl_2$ preferably is added to the buffer as a solution with concentrated HCl. Thereafter, the solution is neutralized such as with sodium hydroxide to attain a pH of between about 4.5 and 8.0, preferably about 5.5. The antibody to anti-CEA (or any other TAA) then is added to the neutralized solution in an amount to attain a concentration of protein up to just less than that which would begin to precipitate the protein in the buffer being used. In order to attain the desired degree of protein labeling, the resultant stannous ion, buffer, protein solution is allowed to incubate. For example, at room temperature, the incubation time should be at least about 15 hours, preferably at least about 20 hours under a nitrogen or an inert gas atmosphere. If desired, this solution can be heated moderately to reduce the incubation time. The solution then can be either freeze-dried and subsequently reconstituted for admixture with pertechnetate or can be admixed directly with pertechnetate solution to obtain the labeled protein. If desired, the resultant radiolabeled protein may be further purified to separate the labeled protein from free technetium such as by chromatography in a Sephadex column. However, this last step is optional.

The present invention also provides a kit with which a user can prepare the composition of this invention and administer it to a patient relatively quickly after preparation. The kit includes each antibody either in lyophilized form, frozen or liquid of suitable ionic strength and pH, and either containing or not containing a reducing agent. If without the reducing agent, the final antibody can be admixed with a reducing solution or solid provided within the kit and in a separate container. Representative, suitable reducing agents are $SnCl_2$ or $SnF_2$ to be dissolved or already dissolved in an appropriate solution, such as sodium acetate/acetic acid, acidified deionized or distilled water, or the like, such that a reducing pH of about 3 to 8.0 is obtained when combined with technetium-99m as sodium pertechnetate. Therefore, technetium-99m as pertechnetate is either reduced in the presence of reducing agent prior to addition of the final antibody or is reduced when added to the final antibody containing reducing agent. The solution of labeled final antibody is then suitable for administration to a patient.

In forming the technetium-labeled products of this invention, a solution of the technetium-99m as the pertechnetate is poured onto the column in order to bind the technetium thereon. A physiologically acceptable aqueous solution of the final antibody then is poured onto the column in order to bind the labeled technetium to the final antibody. The labeled protein then is eluted from the column with saline or an otherwise appropriate buffer and is collected from the bottom of the column in a form suitable for intravenous administration to a patient. In an alternative embodiment, the eluted labeled protein is passed through a bed of anion exchange resin in order to remove free pertechnetate from the labeled protein thereby to form a pure labeled final antibody substantially free of radiochemical contamination. If desired, these anion exchange resins need not be a part of the columns utilized for labeling but can comprise a separate bed through which the labeled protein is passed.

In an alternative embodiment of this invention, the kit can include a container for a column of material which entraps or otherwise binds technetium-99m such as Sephadex, Sepharose or cellulose. The column of this material also can contain the reducing agent for technetium or the reducing agent can be added thereto when it is desired to reduce the technetium. The present invention may also provide a kit which contains each antibody either in lyophilized form, frozen, or liquid of suitable ionic strength and pH with the final antibody being labeled with Tc-99m.

The labeled final antibody is administered by intravenous injection in a pharmaceutically acceptable saline solution, sterile and pyrogen-free. Suitable dosages are usually between about 0.5 and 30 millicuries, preferably between about 10 and 20 millicuries of technetium-99m final antibody for the normal 70 kg patient. The patient then can be scanned by conventional scintigraphy within 1 hour to about 5 days after administration of the labeled protein. Tumors are located in those areas showing a high concentration of labeled final antibody.

It should be understood that the procedure of this invention also can be based upon antigens other than CEA which are tumor associated such as alphafetoprotein antigen or other tumor associated markers wherein one or a series of antibodies are produced as described above and the last produced antibody is radiolabeled.

The following examples illustrate the present invention and are not intended to limit the same.

EXAMPLE I

This example illustrates the preparation of antibody to anti-hCG which can be radiolabeled for use in the present invention in admixture with other antibody to anti-TAA. The anti-hCG (sheep) is obtained from Serono Laboratories, Inc. The last antibody was prepared by injecting rabbits with normal sheep IgG in saline. After allowing for an incubation period, the rabbits were bled and th IgG fraction was recovered by gel chromatography, and purified by affinity chromatography. The IgG fraction was shown to have significant activity as the antibody for sheep IgG by the Ouchterlony immunodiffusion method.

EXAMPLE II

This example illustrates a direct method of labeling to form the antibody to anti-hCG and which can be utilized to label other antibodies to to anti-TAA. The second antibody is obtained by the procedure of Example I. Technetium-99m is obtained from New England Nuclear Corporation.

To 0.4 ml of 50 mM of sodium-potassium tartrate buffer (pH 5.50) (10.51 g/l, pH adjusted to 5.50 with 50 mM tartaric acid is added 1.6 ml of a 50 mM potassium biphthalate buffer (pH 5.50) (10.21 g/l, pH adjusted to 5.50 with 10 N NaOH). To the resultant buffer solution is added 0.02 ml of 0.5 M $SnCl_2$-HCl (94.8 g/l conc. HCl). The resultant solution is titrated back to a pH of $5.65 \pm 0.05$ by adding thereto 0.02 ml of 10 N NaOH and the resultant solution is adjusted to a pH of $5.65 \pm 0.05$ with 1N NaOH. To this solution is added 0.3 ml of a saline solution of the antibody to anti-hCG (10 mg protein/ml saline). The reaction vessel is allowed to stand approximately 21 hours at room temperature under a nitrogen atmosphere. This solution may be freeze-dried to make a $Tc^{99m}$-labeling kit. Thereafter, 0.2 ml of $NaTcO_4$ with an activity of 0.02–20 mCi is added to protein-containing composition and allowed to stand about 1 hour to effect substantially complete labeling of the protein prior to use. The resultant product is passed through a Sephadex column to remove free technetium from the labeled product.

Cancer cells of the type set forth in Table I were reacted in vitro in two steps. (1) Approximately $10^6$ cells were exposed to either normal sheep IgG or sheep anti-hCG (IgG) obtained by the procedure of Example III for thirty minutes at room temperature; cells were then washed three times with a balanced salt solution containing 1% human serum albumin (BSS + 1% HSA) using centrifugation to remove unbound antibody. The cells were then incubated for thirty minutes at room temperature with rabbit anti-sheep IgG labeled with $Tc^{99m}$ obtained by the procedure of Example III; cells were then washed with BSS + 1% HSA solution and cell pellets were subsequently counted for radioactivity using a gamma counter.

In Table I, specific binding ratio is defined as the ratio of hCG specific binding obtained from cancer cells divided by the hCG specific binding obtained from normal cells. Cell suspensions used for binding studies were lysed with the addition of a 1 N NaOH solution. Cell lysates were then quantitated for protein content using 280 nm absorbance via a dual beam spectrophotometer. The concentration of protein (mg/ml) was determined for each cell suspension, in order to correlate the amount of radioactivity (CPM) as a function of cell number. Using this system, it was found that normal human peripheral blood leukocytes had 194 CPM/mg protein of hCG specific binding, whereas normal human bone marrow had hCG specific binding of 201 CPM/mg protein. The average value of these two normal tissues (i.e., 198 CPM/mg protein) was used as the amount of binding to normal tissue. All tumor cell data is expressed as the ratio of hCG specific binding obtained from normal cells (i.e., BeWo had 3.52 times as much activity as did the normal control samples). Those values that are greater than 1.0 indicate preferential uptake of the anti-hCG antibody on tumor cells. Specific binding ratios greater than about 1.25 may be sufficient to localize tumors using gamma scintigraphy.

TABLE I

| Cell Name | Cell Type | $Tc^{99m}$-anti-anti-hCG Specific Binding Ratio |
|---|---|---|
| BeWo | choriocarcinoma | 3.52 |
| JEG | choriocarcinoma | 8.30 |
| HeLa | cervical carcinoma | 2.21 |
| HT-1080 | fibrosarcoma | 4.81 |
| RPMI-8226 | multiple myeloma | 5.04 |
| WI-38 | SV-40 transformed lung | 8.74 |
| HL-60 | acute myeloid leukemia | 4.06 |
| RAJI | Burkitt lymphoma | 2.94 |

As shown in Table I, specific binding ratios greater than 1.25 were obtained for all of the human cell lines tested. Thus, the process of this invention is shown to be useful in selectively identifying cancer cells through the preferential binding of anti-hCG antibodies.

EXAMPLE III

This example illustrates the preparation of heterologous polyclonal antibodies of human tumor associated antigens (TAA). Polyclonal antibodies to hCG (as discussed in Example I), carcinoembryonic antigen (CEA), alphafetoprotein (AFP) and/or other tumor antigens that can be obtained in suitable quantities, may be prepared by immunizing an appropriate species (rabbit, sheep, goat, horse, etc.) with a semi-purified form of the TAA. The TAA may be conjugated to an immunogenic carrier molecule in order to increase the immunogenicity of the TAA. The TAA and/or conjugate is injected intradermally, subcutaneously, intramuscularly or intravenously into the animal with or without adjuvant. After several weeks, the animal is re-exposed to the antigen-conjugate in order to elicit an antibody memory response. Following one or more subsequent immunizations, the serum from the animal is examined for antibodies to the TAA by radioimmunoassay, enzyme-linked immunoassay or any other suitable in vitro technique. Animals found to have a suitable level of antibody in terms of specificity and/or affinity are then bled to recover the heterologous polyclonal antibody. These animals may then be boosted again with the antigen to generate additional antibodies. Antibodies prepared according to this technique may contain suitable reactivity with human TAA, but they may also contain natural or cross-reacting antibodies to normal human antigens not associated with cancer. Therefore, these antibodies are exposed to normal human cells, such as human peripheral blood leukocytes, to remove any antibodies that react with normal cells. Following sequential absorptions of such polyclonal antisera with normal cells, an antibody preparation with suitable specificity for human tumors can be obtained. This antibody may then be purified by gel chromatography, ion exchange chromatography and/or affinity chromatography, and then they may be digested with pepsin to obtain $F(ab')_2$ fragments of high purity antibodies to a variety of different types of TAAs.

An alternative approach to the preparation of heterologous polyclonal antibodies to human TAA is to immunize an appropriate species with a preparation of human tumor cells, tumor cell membranes and/or human tumor cell-free extracts. This approach is used when sufficient quantities of semi-purified human TAA are not available for immunizations. Following immunization of animals with tumor cells or appropriate cell extracts, antisera is obtained and is tested using a cellular assay. That is, antisera are reacted with the type of tumor or tumor cell line that was used for immunization. Binding of the antibody can be detected using a second radiolabeled, fluorescent, enzyme-labeled or other type of second antibody that is reactive with the antisera to TAA and which identified the first antibody on the cell surface. Antibodies obtained by this alternate method may also have to be absorbed using normal cells to remove antibodies to normal tissue antigens, and this antisera can be purified and/or fragmented, as discussed above.

Antibodies that are reactive with anti-TAA can be made by immunizing a different species than used for the first antibody with immunoglobulin of the same type as the first antibody. For example, if an anti-TAA is prepared in a rabbit, the second antibody could be prepared in a sheep using normal rabbit IgG as an immunogen, to obtain sheep anti-rabbit IgG. The second antibody can be radiolabeled with Tc-99m according to Example II, and can be used to detect the presence of the first antibody on human tumor cells. In practice, the two antibodies are injected intravenously into a patient with a suspected malignancy in a series, with the second antibody following the first antibody by several hours to allow for the first antibody to clear the blood stream, permitting the second antibody to bind to the first antibody associated with the tumor cell surface. This binding permits detection of a human tumor in vivo by a procedure that is preferred over a single antibody approach.

EXAMPLE IV

This example illustrates the preparation of murine and/or human monoclonal antibodies to TAA. When the antigen (TAA) is available in an appropriate form and quantity, it can be used directly or in a conjugated form to immunize either mice in vivo or human spleen cells in vitro. Alternatively, whole tumor cells, tumor cell membranes or a tumor cell extract may be used to immunize mice or human spleen cells.

In the formation of murine monoclonal antibodies, spleen cells from immunized mice that are producing antibody to human TAA (such as hCG, CEA, AFP, melanoma associated antigen, neuroblastoma associated antigen, sarcoma associated antigen, breast cancer associated antigen, ovary associated antigen, etc.) are removed from the mouse and are fused with a hypoxanthine-aminopterine-thymidine (HAT) sensitive murine myeloma or other cell lines to form a murine hybridoma that secretes antibody to the TAA. This hybridoma is screened and selected following fusion using in vitro assays that are capable of detecting anti-TAA antibodies. If the antigen is available in sufficient purity and quantity, a radioimmunoassay, enzyme-linked, or other assay can be used for screening clones of murine hybridomas for suitable antibody. Otherwise, whole cell assays can be employed to identify monoclonal anti-TAA. The murine hybridoma is grown in tissue culture or as a murine ascites in vivo to produce sufficient quantities of antibodies for purification and fragmentation, as described.

Human monoclonal antibodies are prepared by immunizing human spleen cells in tissue culture, followed by fusion of the human spleen cells producing anti-TAA with a HAT-sensitive human myeloma or other cell lines. Human hybridomas producing monoclonal anti-TAA antibodies are screened, as discussed above. Human hybridomas producing anti-TAA can be grown in vitro or in vivo in nude mice or in immunosuppressed animals to produce large quantities of antibody that can be purified and fragmented according to procedures discussed previously. Human monoclonal antibodies may have advantages over murine or other species of monoclonal antibodies in that they may not elicit immune responses in patients receiving these immunodiagnostic agents. However, these human monoclonal antibodies may have limitations in that they cannot be generated in high affinity forms. For this reason, human TAA may have to be conjugated to immunogenic foreign proteins in order to generate suitable immune responses in human spleen cells.

Following generation of an appropriate murine or human monoclonal antibody, a second antibody can be made using either polyclonal and/or monoclonal technology. The second antibody must be generated in a sufficiently pure form to permit radiolabeling with Tc-99m, according to Example II. Human or murine monoclonal antibodies may be utilized in a double antibody approach to tumor imaging, according to the procedures described in Example III. Table II illustrates the use of an anti-melanoma associated antigen monoclonal antibody obtained from a murine hybridoma, and a Tc-99m labeled goat anti-mouse IgG antibody in identifying human TAA in vitro. As shown, there is a significant amount of binding of the double antibody composition to the melanoma cell lines, but not to the erythroleukemia cell line. This table illustrates that specific antibodies to TAA can be prepared that can have selective reactivity with human tumors. The double antibody approach here illustrated in vitro has advantages in in vivo use in that it provides increased sensitivity for tumor detection.

TABLE II

| Tc-99m Double Antibody Binding to Human Tumor Cell Lines[a] | | | |
|---|---|---|---|
| Cell Line | Types of Tumor | Antibody | % Specific Binding[b] |
| Colo-38 | Melanoma | $MoAb_1$[c] | 13.06 |
| | | $MoAb_2$ | 13.96 |
| M-16 | Melanoma | $MoAb_1$ | 17.0 |
| | | $MoAb_2$ | 16.3 |
| M-21 | Melanoma | $MoAb_1$ | 13.7 |
| | | $MoAb_2$ | 14.0 |
| K-562 | Erythroleukemia | $MoAb_1$ | 0.02 |
| | | $MoAb_2$ | 0 |

[a]Binding performed in vitro using $10^6$ human tumor cells.
[b]Specific binding is calculated as the total percentage of radioactivity associated with antibody added to the cells, less the amount of binding of an appropriate nonimmune antibody (in this case - a nonimmune mouse) $IgG_{2a}$.
[c]Monoclonal antibodies 1 and 2 that are reactive with human melanoma associated antigens.

I claim:

1. A composition of matter comprising a radiolabeled antibody, said radiolabeled antibody either:

(a) being directly reactive with *an antibody to* a tumor associated antigen; or (b) being reactive with a second antibody which is directly reactive with said antigen, said reactivity with said second antibody either being direct or through a series of at least one third antibody, the last of said series being directly reactive with said second antibody, said radiolabel consisting of technetium-99m.

2. The composition of claim 1 wherein said antigen is carcinoembryonic antigen.

3. The composition of claim 1 wherein said antigen is alphafetoprotein.

4. The composition of claim 1 wherein said antigen is human melanoma associated antigen.

5. The composition of claim 1 wherein said antigen is human neuroblastoma antigen.

6. The composition of claim 1 wherein said antigen is human breast cancer associated antigen.

7. The composition of claim 1 wherein said antigen is human carcinoma associated antigen.

8. The composition of claim 1 wherein said antigen is human ovary associated antigen.

9. The composition of claim 1 wherein said antigen is human sarcoma associated antigen.

10. The composition of any one of claims 1, 2, 3, 4, 5, 6, 7, 8 or 9 wherein said radiolabeled antibody is directly reactive with said antigen.

11. The process of detecting cancer cells and/or a malignant tumor in a human which comprises injecting into the human an antibody to a tumor associated antigen, subsequently injecting into the human the series of antibodies of claim 1 in the sequence said antibodies are produced with the last of said injected antibodies being said labeled antibody, the time between injections being sufficient to allow substantially all of said antigen and said antibodies not bound to said cells and/or tumor to be metabolized and monitoring the biodistribution of the radiolabeled antibody in said human.

12. The process of claim 11 wherein the tumor associated antigen is the composition of claim 2.

13. The process of claim 11 wherein the tumor associated antigen is the composition of claim 3.

14. The process of claim 11 wehrein the tumor associated antigen is the composition of claim 4.

15. The process of claim 11 wherein the tumor associated antigen is the composition of claim 5.

16. The process of claim 11 wherein the tumor associated antigen is the composition of claim 6.

17. The process of claim 11 wherein the tumor associated antigen is the composition of claim 7.

18. The process of claim 11 wherein the tumor associated antigen is the composition of claim 8.

19. The process of claim 11 wherein the tumor associated antigen is the composition of claim 9.

20. The process of any one of claims 11, 12, 13, 14, 15, 16, 17, 18 or 19 wherein said radiolabeled antibody is directly reactive with said antigen.

21. A diagnostic kit suitable for forming a composition useful in identifying a cancer cell and/or a malignant tumor which comprises a sterile package containing an antibody either:

(a) being directly reactive with *an antibody to* a tumor associated antigen; or (b) being reactive with a second antibody which is directly reactive with said antigen, said reactivity with said second antibody either being direct or through a series of at least one third antibody, a package sterilized reducing agent for technetium, and means for mixing the contents of said sterile package with said reducing agent for technetium-99m in a physiologically acceptable aqueous solution.

22. The kit of claim 21 wherein a physiologically acceptable reducing agent useful in reducing technetium (VII) to the technetium (IV) state is admixed with said protein.

23. The kit of claim 21 wherein said protein in said sterile package is lyophilized.

24. The kit of claim 22 wherein said protein and reducing agent are lyophilized.

25. The kit of claim 21 which includes a column of material for binding technetium in the IV state and of releasing said technetium when contacted with a solution of said antibody.

26. The kit of claim 23 which includes an ionic exchange resin for selectively removing pertechnetate ion from a solution containing pertechnetate ion from a protein labeled with technetium-99m.

27. The kit of any one of claims 21, 22, 23, 24, 25 or 26 wherein said tumor associated antigen is carcinoembryonic antigen.

28. The kit of any one of claims 21, 22, 23, 24, 25 or 26 wherein said tumor associated antigen is alphafetoprotein.

29. The kit of any one of claims 21, 22, 23, 24, 25 or 26 wherein said tumor associated antigen is human melanoma associated antigen.

30. The kit of any one of claims 21, 22, 23, 24, 25 or 26 wherein said tumor associated antigen is human neuroblastoma antigen.

31. The kit of any one of claims 21, 22, 23, 24, 25 or 26 wherein said tumor associated antigen is human breast cancer associated antigen.

32. The kit of any one of claims 21, 22, 23, 24, 25 or 26 wherein said tumor associated antigen is human carcinoma associated antigen.

33. The kit of any one of claims 21, 22, 23, 24, 25 or 26 wherein said tumor associated antigen is human ovary associated antigen.

34. The kit of any one of claims 21, 22, 23, 24, 25 or 26 wherein said tumor associated antigen is human sarcoma associated antigen.

* * * * *